(12) United States Patent
Nakanami et al.

(10) Patent No.: US 10,308,408 B2
(45) Date of Patent: Jun. 4, 2019

(54) PACKAGING FOR ADHESIVE PATCH CONTAINING RIVASTIGMINE

(71) Applicant: NICHIBAN CO., LTD., Tokyo (JP)

(72) Inventors: Shuta Nakanami, Tokyo (JP); Kanako Inagaki, Tokyo (JP)

(73) Assignee: NICHIBAN CO., LTD., Tokyo (JP)

( * ) Notice: Subject to any disclaimer, the term of this patent is extended or adjusted under 35 U.S.C. 154(b) by 154 days.

(21) Appl. No.: 15/310,412

(22) PCT Filed: May 14, 2015

(86) PCT No.: PCT/JP2015/063936
§ 371 (c)(1),
(2) Date: Nov. 10, 2016

(87) PCT Pub. No.: WO2015/174502
PCT Pub. Date: Nov. 19, 2015

(65) Prior Publication Data
US 2017/0152089 A1 Jun. 1, 2017

(30) Foreign Application Priority Data

May 15, 2014 (JP) .................................. 2014-101179
Sep. 25, 2014 (JP) .................................. 2014-195598

(51) Int. Cl.
| | | |
|---|---|---|
| *B32B 7/04* | (2019.01) | |
| *B65D 65/40* | (2006.01) | |
| *A61J 1/00* | (2006.01) | |
| *A61K 31/27* | (2006.01) | |
| *B32B 27/28* | (2006.01) | |
| *B65D 77/00* | (2006.01) | |
| *A61K 9/70* | (2006.01) | |
| *B65B 7/02* | (2006.01) | |
| *B65B 31/00* | (2006.01) | |
| *B32B 15/08* | (2006.01) | |
| *B32B 15/082* | (2006.01) | |
| *B32B 15/085* | (2006.01) | |
| *B32B 15/088* | (2006.01) | |
| *B32B 15/09* | (2006.01) | |
| *B32B 15/12* | (2006.01) | |
| *B32B 15/20* | (2006.01) | |
| *B32B 27/08* | (2006.01) | |
| *B32B 27/30* | (2006.01) | |
| *B32B 27/32* | (2006.01) | |
| *B32B 27/34* | (2006.01) | |
| *B32B 27/36* | (2006.01) | |
| *B65B 5/04* | (2006.01) | |

(Continued)

(52) U.S. Cl.
CPC ................ *B65D 65/40* (2013.01); *A61J 1/00* (2013.01); *A61K 9/7007* (2013.01); *A61K 9/7061* (2013.01); *A61K 31/27* (2013.01); *B32B 7/04* (2013.01); *B32B 15/08* (2013.01); *B32B 15/082* (2013.01); *B32B 15/085* (2013.01); *B32B 15/088* (2013.01); *B32B 15/09* (2013.01); *B32B 15/12* (2013.01); *B32B 15/20* (2013.01); *B32B 27/08* (2013.01); *B32B 27/28* (2013.01); *B32B 27/281* (2013.01); *B32B 27/302* (2013.01); *B32B 27/306* (2013.01); *B32B 27/308* (2013.01); *B32B 27/32* (2013.01); *B32B 27/34* (2013.01); *B32B 27/36* (2013.01); *B32B 27/365* (2013.01); *B65B 7/02* (2013.01); *B65B 31/00* (2013.01); *B65D 77/00* (2013.01); *B32B 2250/03* (2013.01); *B32B 2250/04* (2013.01); *B32B 2307/31* (2013.01); *B32B 2307/714* (2013.01); *B32B 2307/7244* (2013.01); *B32B 2307/748* (2013.01); *B32B 2439/46* (2013.01); *B32B 2439/80* (2013.01); *B65B 5/045* (2013.01); *B65B 31/04* (2013.01); *B65B 51/10* (2013.01); *B65D 77/04* (2013.01); *B65D 81/2084* (2013.01); *B65D 81/266* (2013.01)

(58) Field of Classification Search
USPC ......... 206/438, 439, 440, 441, 484.1, 484.2, 206/484
See application file for complete search history.

(56) References Cited

U.S. PATENT DOCUMENTS

| | | |
|---|---|---|
| 6,335,031 B1 | 1/2002 | Asmussen et al. |
| 2001/0048938 A1 | 12/2001 | Asmussen et al. |
| 2007/0128263 A1 | 6/2007 | Gargiulo et al. |
| 2011/0066120 A1 | 3/2011 | Lee |

(Continued)

FOREIGN PATENT DOCUMENTS

| | | |
|---|---|---|
| EP | 2172194 B1 | 10/2010 |
| JP | 2002-500178 A | 1/2002 |

(Continued)

*Primary Examiner* — Jacob K Ackun
(74) *Attorney, Agent, or Firm* — Porter Wright Morris & Arthur LLP

(57) ABSTRACT

To provide a packaging for a rivastigmine-containing adhesive patch having excellent temporal stability of rivastigmine, an adhesive patch product including the adhesive patch and a packaging bag, and a method for manufacturing the same.
An adhesive patch product including a packaging bag formed from a laminate of at least three layers including an ethylene-vinyl alcohol copolymer film and a rivastigmine-containing adhesive patch housed in the packaging bag and having a residual oxygen concentration of 10% by volume or less in the packaging bag, and a method for manufacturing the same are provided. In addition, a packaging for a rivastigmine-containing adhesive patch formed from a laminate including an ethylene-vinyl alcohol copolymer film and having a residual oxygen concentration of 10% by volume or less therein is provided.

7 Claims, No Drawings

(51) Int. Cl.
*B65B 51/10* (2006.01)
*B65D 81/20* (2006.01)
*B65D 81/26* (2006.01)
*B65B 31/04* (2006.01)
*B65D 77/04* (2006.01)

(56) References Cited

U.S. PATENT DOCUMENTS

| | | | |
|---|---|---|---|
| 2011/0290694 A1* | 12/2011 | Fuisz | A61J 3/00 206/459.5 |
| 2012/0031047 A1 | 2/2012 | Shinoda et al. | |
| 2013/0220846 A1* | 8/2013 | Hiraoka | A61K 31/27 206/213.1 |
| 2013/0261571 A1 | 10/2013 | Prinz et al. | |
| 2013/0266520 A1* | 10/2013 | Fuisz | A61J 3/00 424/10.2 |
| 2014/0076763 A1* | 3/2014 | Kimball | A61F 13/00063 206/440 |
| 2014/0083890 A1* | 3/2014 | Ishizaki | A61K 9/7038 206/438 |
| 2014/0262883 A1* | 9/2014 | Devouassoux | A61M 5/002 206/364 |
| 2014/0303574 A1* | 10/2014 | Knutson | A61F 13/0008 604/307 |
| 2015/0224247 A1* | 8/2015 | McDorman | A61M 5/003 206/569 |

FOREIGN PATENT DOCUMENTS

| | | |
|---|---|---|
| JP | 2009-517468 A | 4/2009 |
| JP | 2012-051875 A | 3/2012 |
| JP | 2012-116956 | 6/2012 |
| WO | 2011/076621 A2 | 6/2011 |
| WO | 2013/128562 A1 | 9/2013 |

* cited by examiner

PACKAGING FOR ADHESIVE PATCH CONTAINING RIVASTIGMINE

TECHNICAL FIELD

The present invention relates to a packaging of an adhesive patch and a method for packaging an adhesive patch, and specifically relates to a packaging of an adhesive patch capable of suppressing temporal reduction of a drug content in a rivastigmine-containing adhesive patch by disposing an ethylene-vinyl alcohol copolymer (hereinafter, also referred to as EVOH) film layer in a packaging material when the rivastigmine-containing adhesive patch is packaged with a packaging, and a method for manufacturing the packaging of an adhesive patch.

Rivastigmine is one of acetylcholinesterase inhibitors, and has been used as a therapeutic agent for Alzheimer type dementia (anti-dementia drug).

As for these anti-dementia drugs, in addition to oral administration such as a tablet, a capsule, syrup, or a granule, injection administration and rectal administration have been studied according to a drug or conditions of a disease. In recent years, transdermal administration, that is, administration using an adhesive patch has been proposed.

It has been pointed out that rivastigmine is relatively easily oxidized and has a risk to increase a decomposed product over time. Therefore, a method for blending an antioxidant in a rivastigmine-containing adhesive patch has been proposed (Patent Literatures 1 and 2, and the like). Patent Literature 2 has reported a formulation obtained by bonding a rivastigmine-containing storage layer and a silicone adhesive. However, the silicone adhesive itself has high cost, and a release liner needs to be subjected to a special treatment. Therefore, cost is increased disadvantageously.

The adhesive patch proposed in Patent Literature 1 or 2 uses a carboxyl group-containing acrylic adhesive. However, this use gives not a small effect on oxidation of rivastigmine. Therefore, there has been a report that an adhesive patch having excellent temporal stability of rivastigmine can be obtained by using an adhesive having no carboxyl group or hydroxyl group as an acrylic adhesive (Patent Literature 3).

On the other hand, an adhesive patch using an acrylic rubber hybrid adhesive having a hydroxy group (Patent Literature 4) and an adhesive patch containing a non-volatile substance such as citric acid in an acrylic adhesive layer having a hydroxy group or the like in order to reduce loss of an active substance (drug) due to volatilization thereof in a manufacturing process (Patent Literature 5) have been proposed from a viewpoint of improving skin permeability of rivastigmine or reducing skin irritation in an adhesive layer. However, in these literatures, stability of rivastigmine has not been discussed.

CITATION LIST

Patent Literature

Patent Literature 1: JP 2002-500178 A
Patent Literature 2: JP 2009-517468 A
Patent Literature 3: WO 2011/076621 A
Patent Literature 4: US 2011/0066120 A
Patent Literature 5: EP 2172194 B

SUMMARY OF INVENTION

Technical Problem

As described above, use of an adhesive having no antioxidant blended therein or having no carboxyl group or hydroxy group has been proposed from a viewpoint of eliminating temporal instability due to oxidation of rivastigmine. On the other hand, a packaging container itself for housing a rivastigmine-containing adhesive patch has not been necessarily studied sufficiently.

Solution to Problem

The present inventors have made intensive studies in order to solve the above problems, and studied a configuration of a packaging material having excellent temporal stability of a rivastigmine-containing adhesive patch. As a result, the present inventors have found that, in a packaging bag for housing a rivastigmine-containing adhesive patch, the above problems can be solved by employing a laminate of at least three layers including an ethylene-vinyl alcohol copolymer (EVOH) film and controlling a residual oxygen concentration in the packaging bag, and have completed the present invention.

An embodiment of the present invention provides the following adhesive patch product.

(1) An adhesive patch product including a packaging bag and a rivastigmine-containing adhesive patch housed in the packaging bag, in which the packaging bag is formed from a laminate of at least three layers including an ethylene-vinyl alcohol copolymer film, the laminate has a lamination configuration having a heat-sealable ethylene-vinyl alcohol copolymer film as an innermost layer of the packaging bag, an oxygen blocking layer as a layer outside the ethylene-vinyl alcohol copolymer film, and an outer layer as a layer outside the oxygen blocking layer, or the laminate has a lamination configuration having a sealant layer as an innermost layer of the packaging bag, an ethylene-vinyl alcohol copolymer film as a layer outside the sealant layer, an oxygen blocking layer as a layer outside the ethylene-vinyl alcohol copolymer film, and an outer layer as a layer outside the oxygen blocking layer, and a residual oxygen concentration in the packaging bag is 10% by volume or less.

(2) The adhesive patch product described in (1), in which, in the ethylene-vinyl alcohol copolymer film contained in the laminate, the content of an ethylene unit in the ethylene-vinyl alcohol copolymer is from 10% to 50% by mol.

(3) The adhesive patch product described in (1), in which the adhesive patch includes a support, a rivastigmine-containing drug storage layer disposed on at least one surface of the support, an adhesive layer disposed on the drug storage layer, and release paper disposed on the adhesive layer, or includes a support, an adhesive layer disposed on at least one surface of the support, a rivastigmine-containing drug storage layer disposed on the adhesive layer, and release paper disposed on the drug storage layer, or includes a support, a rivastigmine-containing adhesive layer disposed on at least one surface of the support, and release paper disposed on the rivastigmine-containing adhesive layer.

(4) The adhesive patch product described in (3), in which, in the adhesive patch, the content of rivastigmine in the rivastigmine-containing drug storage layer is from 10% to 40% by mass based on a total mass of the drug storage layer and the adhesive layer, or the content of rivastigmine in the rivastigmine-containing adhesive layer is from 10% to 40% by mass based on a total mass of the rivastigmine-containing adhesive layer.

(5) The adhesive patch product described in (3), in which the adhesive layer or the rivastigmine-containing adhesive layer contains an acrylic adhesive.

Another embodiment of the present invention provides the following packaging.

(6) A packaging for a rivastigmine-containing adhesive patch, in which the packaging is formed from a laminate of at least three layers including an ethylene-vinyl alcohol copolymer film, the laminate has a lamination configuration having a heat-sealable ethylene-vinyl alcohol copolymer film as an innermost layer of the packaging, an oxygen blocking layer as a layer outside the ethylene-vinyl alcohol copolymer film, and an outer layer as a layer outside the oxygen blocking layer, or the laminate has a lamination configuration having a sealant layer as an innermost layer of the packaging, an ethylene-vinyl alcohol copolymer film as a layer outside the sealant layer, an oxygen blocking layer as a layer outside the ethylene-vinyl alcohol copolymer film, and an outer layer as a layer outside the oxygen blocking layer, and a residual oxygen concentration in the packaging is 10% by volume or less.

An embodiment of the present invention provides a method for manufacturing the above adhesive patch product.

(7) A method for manufacturing the adhesive patch product described in (1), including:

a step of preparing a laminate including an ethylene-vinyl alcohol copolymer film and having a heat-sealable layer on a surface layer thereof;

a step of laminating two of the laminates such that the heat-sealable layers face each other and heat-sealing the laminated laminate to manufacture a bag-shaped product having an opening;

a step of introducing a rivastigmine-containing adhesive patch into the bag-shaped product from the opening;

a step of replacing an inside of the bag-shaped product with nitrogen and/or introducing an oxygen absorbent into the bag-shaped product from the opening; and a step of heat-sealing the opening of the bag-shaped product to manufacture an adhesive patch-containing packaging bag.

(8) The method for manufacturing an adhesive patch product described in (7), further including, before the step of heat-sealing the opening of the bag-shaped product to manufacture an adhesive patch-containing packaging bag, a step of discharging gas in the bag-shaped product to an outside by passing between rolls, pressing, or suction degassing as the two laminates sandwich the adhesive patch tightly.

(9) A method for manufacturing the adhesive patch product described in (1), including:

a step of preparing two laminates each including an ethylene-vinyl alcohol copolymer film and each having a heat-sealable layer on a surface layer thereof;

a step of disposing a rivastigmine-containing adhesive patch on the heat-sealable layer of one laminate;

a step of disposing the other laminate on one laminate such that the heat-sealable layers thereof face each other through the adhesive patch;

a step of heat-sealing a most part of the two facing heat-sealable layers while forming an opening by partially not heat-sealing the two facing heat-sealable layers;

a step of replacing an atmosphere around the adhesive patch formed of the two laminates with nitrogen and/or inserting an oxygen absorbent into the vicinity of the adhesive patch; and a step of heat-sealing the opening to manufacture an adhesive patch-containing packaging bag.

(10) The method for manufacturing an adhesive patch product described in (9), further including, before the step of heat-sealing the opening to manufacture an adhesive patch-containing packaging bag, a step of discharging gas around the adhesive patch to an outside from the opening by passing between rolls, pressing, or suction degassing as the two laminates sandwich the adhesive patch tightly.

Advantageous Effects of Invention

By forming a packaging bag for housing a rivastigmine-containing adhesive patch from a laminate of at least three layers including an ethylene-vinyl alcohol copolymer film and making a residual oxygen concentration in the bag 10% by volume or less, the present invention suppresses oxidation of rivastigmine, suppresses generation of a decomposed product, and can reduce temporal reduction of a drug content even without forming an adhesive layer in an adhesive patch with a specific adhesive or adding an antioxidant to the adhesive layer.

DESCRIPTION OF EMBODIMENTS

<Adhesive Patch Product>

The present invention relates to an adhesive patch product including a packaging bag and a rivastigmine-containing adhesive patch housed in the packaging bag.

As described above, the rivastigmine-containing adhesive patch to which the present invention is directed is relatively easily oxidized, and therefore is preferably housed in a packaging bag formed of a packaging material having a high sealing property or a high light-shielding property and stored until just before being used.

The present invention employs an ethylene-vinyl alcohol copolymer (hereinafter, also referred to as EVOH) film capable of suppressing adsorption of rivastigmine as an essential configuration in a laminate to constitute a packaging material. Furthermore, the adhesive patch is enclosed in a packaging bag formed of the packaging material while a residual oxygen concentration in the packaging bag is 10% by volume or less.

<Packaging Bag>

A packaging bag used in the present invention is formed from a laminate of at least three layers including an ethylene-vinyl alcohol copolymer (hereinafter, also referred to as EVOH) film.

The above laminate has any one of the following lamination configurations.

(a) A lamination configuration having a heat-sealable ethylene-vinyl alcohol copolymer film as an innermost layer of the packaging bag, an oxygen blocking layer as a layer outside the ethylene-vinyl alcohol copolymer film, and an outer layer as a layer outside the oxygen blocking layer.

(b) A lamination configuration having a sealant layer as an innermost layer of the packaging bag, an ethylene-vinyl alcohol copolymer film as a layer outside the sealant layer, an oxygen blocking layer as a layer outside the ethylene-vinyl alcohol copolymer film, and an outer layer as a layer outside the oxygen blocking layer.

The innermost layer of the packaging bag is a heat-sealable layer, that is, a heat-sealable EVOH film (refer to description below) or a sealant layer.

The sealant layer can be formed of a conventionally known sealant resin film. However, EVOH is disposed in adjacent to the sealant layer. Therefore, even when the sealant layer has drug permeability, EVOH can suppress a drug adsorption property. Therefore, it is not necessary for the sealant layer to have drug non-permeability. Therefore, as the sealant layer, a material having a high drug non-adsorption capability in addition to easiness of heat-sealing is selected. Examples of the sealant layer include a polyethylene resin film such as a low density polyethylene (LDPE), a linear low density polyethylene (L-LDPE), or a high density polyethylene (HDPE); a polyolefin resin film such as an acid-modified polyethylene, polypropylene, an acid-modified polypropylene, a copolymer polypropylene, an ethylene-vinyl acetate copolymer (EVA), an ethylene-(meth)acrylate copolymer, or an ethylene-(meth)acrylic acid copolymer; and a polyester resin film such as polyethylene terephthalate (PET). However, considering a heat-sealing property and a drug non-adsorption capability, an unstretched polypropylene resin (hereinafter, also referred to as PP) is particularly preferable. When a PP film is used as the innermost layer, PP and EVOH can be laminated directly with each other, or can be laminated through an adhesive having a low rivastigmine adsorption property. For EVOH in this case, it is not necessarily necessary to consider a heat-sealing property. Therefore, the content of an ethylene unit in EVOH can be from 10% to 90% by mol. The sealant layer has a minimum thickness with which a sealed packaging bag can be manufactured by heat-sealing. The thickness is from 10 μm to 50 μm, for example, preferably 30 μm.

In the EVOH film, the content of an ethylene unit in EVOH is preferably from 10% to 50% by mol due to a high heat-sealing property and a high drug (rivastigmine) non-adsorption capability. When the content of an ethylene unit in EVOH is 10% by mol or less, a heat-sealing property cannot be obtained. When the content of an ethylene unit of EVOH is 50% by mol or more, a drug non-adsorption capability is reduced. Therefore, particularly when the EVOH film is used as the innermost layer, the content of an ethylene unit in EVOH is preferably within the above numerical range. The content of water in EVOH (a value with respect to a total mass of EVOH) is preferably 1% by mass or less considering holding a gas barrier property, preventing generation of poor appearance (whitening, foaming, or the like) in a heat-sealing part, and the like. The EVOH film has a minimum thickness with which a sealed packaging bag can be manufactured by heat-sealing. The thickness is from 10 μm to 50 μm, for example, preferably 30 μm.

The oxygen blocking layer disposed outside the EVOH film is only required to be a material capable of blocking incorporation of oxygen form an outside of the packaging bag. Examples thereof include a soft metal foil such as an aluminum foil, and a vapor deposition layer such as aluminum vapor deposition, silica vapor deposition, alumina vapor deposition, or silica-alumina binary vapor deposition.

As the outer layer disposed outside the oxygen blocking layer, a material having a mechanical strength and size stability is preferably employed. Examples of the material include a resin film. Examples thereof include a polyester resin film such as polyethylene terephthalate (PET), polyethylene naphthalate (PEN), or polylactic acid (PLA); a polyolefin resin film such as polypropylene; a polystyrene resin film; a polyamide resin film such as 6-nylon or poly-p-xylyleneadipamide (MXD6 nylon); a polycarbonate resin film; a polyacrylonitrile resin film; and a polyimide resin film. Furthermore, a paper layer such as paper or synthetic paper may be employed as the outer layer.

In addition, as the outer layer, a multi-layer body of the above resin films (for example, nylon 6/MXD/nylon 6, nylon 6/ethylene-vinyl alcohol copolymer/nylon 6), a mixed body thereof, or the like may be used.

The packaging bag used in the present invention is formed of a laminate of at least three layers including an ethylene-vinyl alcohol copolymer (EVOH) film. The laminate only needs to have the above (a) or (b) lamination configuration, and may have a lamination configuration including an additional layer, if necessary.

As the additional layer, examples of a packaging material having a high sealing property or a high light-shielding property, which can be used as a layer configuration of the packaging bag include a polyolefin resin film such as a polyethylene film, a polypropylene film, or a polymethyl pentene film; a vinyl resin film such as a polyvinyl chloride film, a polyvinylidene chloride film, a polyvinyl alcohol film, a polystyrene film, a polyacrylonitrile film, or an ionomer film; a polyester resin film such as a polyethylene terephthalate film; a polyamide resin film such as a nylon film; a cellulosic resin film such as cellophane; a polycarbonate resin film; and a laminated film thereof. Examples of a packaging material for increasing a light-shielding property in addition to a shielding property include a laminated film of the above resin films, a laminated film thereof, and a soft aluminum foil (hereinafter, also abbreviated as AL), and a pigment-added resin film obtained by adding a black pigment or the like to the above resin films. In the additional layer, the resin films, the laminated films, and the like can be variously combined with one another to be used as a laminate.

As the additional layer, a film or a sheet including a layer containing an oxygen adsorbent can be disposed. An oxygen absorbent is not particularly limited. However, examples thereof include an inorganic oxide, a mixture containing an electrolyte, a reducing inorganic salt, a polyphenol, a reducing sugar, a reducing agent, an unsaturated fatty acid compound, an unsaturated organic compound, a thermoplastic polymer, a composition containing an oxygen absorption-promoting substance, and a mixture thereof. Examples of a packaging material containing an oxygen absorbent include oxy guard (registered trademark) (manufactured by Toyo Seikan Co.) and oxy catch (registered trademark) (manufactured by Kyodo Printing Co.).

Specific examples of a lamination configuration of a preferable laminate used for the packaging bag of the present invention include a configuration of PP/EVOH/AL/polyester and a configuration of EVOH/AL/polyester from the innermost layer of the packaging bag.

The above laminate can be manufactured by dry lamination, extrusion lamination, or co-extrusion lamination. The thickness of the laminate can be about from 10 μm to 100 μm. The respective layers are laminated directly or through an adhesive or the like. When layers are bonded to each other with an adhesive, an adhesive having less drug adsorption is desirably used. For example, an isocyanate such as TDI or MDI can be used as an adhesive, or a polyurethane adhesive including a polyol or the like can be used. The packaging is formed so as to have a size slightly larger than the rivastigmine-containing adhesive patch. The size of the packaging is preferably 1.5 times to 10 times that of the adhesive patch. For example, in a case of an adhesive patch having a size of 3 cm (vertical)×3 cm (horizontal), the packaging can have a size of 6 cm (vertical)×6 cm (horizontal). Like the adhesive patch, R can be put by cutting a corner roundly. The area of the adhesive patch can be determined appropriately. However, the area is preferably from 2 cm$^2$ to 25 cm$^2$ in order to minimize the amount adhering to a support due to volatilization of a drug in packaging material and to obtain adhesion easiness.

In the adhesive patch product of the present invention, a residual oxygen concentration is 10% by volume or less in the packaging bag formed from the above laminate.

Specific methods for making the residual oxygen concentration in the packaging bag 10% by volume or less include (I) a method for replacing and filling an atmosphere in the packaging bag with nitrogen using a vacuum gas packaging machine or the like, (II) a method for using the film or sheet including a layer containing an oxygen adsorbent as a layer to constitute the laminate of the packaging bag, and (III) a method for causing an oxygen adsorbent to exist in the packaging bag while the oxygen adsorbent is enclosed separately.

Among these methods, it is preferable to make the residual oxygen concentration in the packaging bag 10% by volume or less by (I) replacing and filling an atmosphere in the packaging bag with nitrogen using a vacuum gas packaging machine or the like from a viewpoint of stability of rivastigmine.

Specifically, an adhesive patch is housed in a packaging bag produced from the above laminate, the residual oxygen concentration in the packaging bag is caused to become 10% by volume or less, and then the packaging bag is sealed by a known method such as heat-sealing to store the adhesive patch product of the present invention. At this time, a heat-sealing width can be determined appropriately, but is preferably about from 2 mm to 20 mm.

When a plastic laminate film material containing aluminum is employed in the laminate to constitute the packaging bag of the present invention, a V-shaped notch or an I-shaped notch is preferably disposed on a heat-sealed surface (innermost layer) because it is difficult to open the packaging bag with hands due to high tear strength of the plastic laminate film.

<Packaging>

The present invention is also directed to a packaging for a rivastigmine-containing adhesive patch. That is, the present invention is also directed to a packaging formed from a laminate of at least three layers including an ethylene-vinyl alcohol copolymer film. The laminate has a lamination configuration having a heat-sealable ethylene-vinyl alcohol copolymer film as an innermost layer of the packaging, an oxygen blocking layer as a layer outside the ethylene-vinyl alcohol copolymer film, and an outer layer as a layer outside the oxygen blocking layer, or a lamination configuration having a sealant layer as an innermost layer of the packaging, an ethylene-vinyl alcohol copolymer film as a layer outside the sealant layer, an oxygen blocking layer as a layer outside the ethylene-vinyl alcohol copolymer film, and an outer layer as a layer outside the oxygen blocking layer. A residual oxygen concentration in the packaging is 10% by volume or less.

Here, as the laminate to constitute the packaging, a laminate having the same lamination configuration as the laminate used for the above packaging bag of the adhesive patch product can be employed. As a method for making a residual oxygen concentration 10% by volume or less, the above methods (I) to (III) can be employed.

<Method for Manufacturing Adhesive Patch Product>

A method for manufacturing the adhesive patch product of the present invention is not particularly limited. However, for example, the method is roughly classified into the following two steps. A laminate used in [1] and [2] has the same lamination configuration as the laminate used for the above packaging bag of the adhesive patch product.

[1] A step of preparing a laminate including an ethylene-vinyl alcohol copolymer film and having a heat-sealable layer on a surface layer thereof, a step of laminating two of the laminates such that the heat-sealable layers face each other and heat-sealing the laminated laminate to manufacture a bag-shaped product having an opening, a step of introducing a rivastigmine-containing adhesive patch into the bag-shaped product from the opening;

a step of replacing an inside of the bag-shaped product with nitrogen and/or introducing an oxygen absorbent into the bag-shaped product from the opening;

a step of discharging gas (oxygen, nitrogen, or the like) in the bag-shaped product to an outside by passing between rolls, pressing, or suction degassing such that the two laminates sandwich the adhesive patch tightly (optional step), and a step of heat-sealing the opening of the bag-shaped product to manufacture an adhesive patch-containing packaging bag.

[2] A step of preparing two laminates each including an ethylene-vinyl alcohol copolymer film and each having a heat-sealable layer on a surface layer thereof, a step of disposing a rivastigmine-containing adhesive patch on the heat-sealable layer of one of the laminates, a step of disposing the other one of the laminates on the one of the laminates such that the heat-sealable layers thereof face each other through the adhesive patch, a step of heat-sealing a most part of the two facing heat-sealable layers and forming an opening without heat-sealing a part thereof, a step of replacing an atmosphere around the adhesive patch formed of the two laminates with nitrogen and/or inserting an oxygen absorbent into the vicinity of the adhesive patch, a step of discharging gas (oxygen, nitrogen, or the like) around the adhesive patch to an outside from the opening by passing between rolls, pressing, or suction degassing such that the two laminates sandwich the adhesive patch tightly (optional step), and a step of heat-sealing the opening to manufacture an adhesive patch-containing packaging bag.

In the manufacturing method [2], in order to replace an atmosphere around the adhesive patch with nitrogen, in the series of manufacturing steps, for example, when a heat-sealing operation is performed, by covering the step itself in which the operation is performed with a box or the like and filling an inside of the box with nitrogen, an atmosphere in the packaging bag can be replaced with nitrogen.

In addition, the oxygen absorbent may be introduced simultaneously with introduction of the rivastigmine-containing adhesive patch, or before or after introduction of the rivastigmine-containing adhesive patch. When replacement with nitrogen is further performed, the oxygen absorbent may be introduced after replacement with nitrogen.

In the manufacturing method [1] or [2], before the opening is heat-sealed, a step of discharging gas (oxygen, nitrogen, or the like) in the bag-shaped product ([1]) or around the adhesive patch ([2]) to an outside by passing between rolls (an operation to cause the bag-shaped product ([1]) or the two laminates ([2]) sandwiching the adhesive patch to pass between two rolls), pressing, or suction degassing such that the two laminates sandwich the adhesive patch tightly can be performed as an optional step. When a volatile substance exists in the bag-shaped product, gas is preferably as little as possible. Therefore, in this case, this step is preferably performed.

<Rivastigmine-Containing Adhesive Patch>

The rivastigmine-containing adhesive patch (hereinafter, also simply referred to as an adhesive patch) to which the present invention is directed will be described in detail below.

The above adhesive patch preferably has the following configurations (i) to (iii).

(i) An adhesive patch including a support, a rivastigmine-containing drug storage layer disposed on at least one surface of the support, an adhesive layer disposed on the drug storage layer, and release paper disposed on the adhesive layer.

(ii) An adhesive patch including a support, an adhesive layer disposed on at least one surface of the support, a rivastigmine-containing drug storage layer disposed on the adhesive layer, and release paper disposed on the drug storage layer.

(iii) An adhesive patch including a support, a rivastigmine-containing adhesive layer disposed on at least one surface of the support, and release paper disposed on the rivastigmine-containing adhesive layer.

[Support]

Examples of the support used for the adhesive patch to which the present invention is directed include a flexible support such as a film, a nonwoven fabric, Japanese paper, a cotton fabric, a knitted fabric, a woven fabric, or a laminate composite of a nonwoven fabric and a film. As a material for these supports, a material having such a flexibility as to be able to adhere to the skin closely and to follow movement of the skin, and a material capable of suppressing occurrence of skin rash or the like after long-term adhesion are preferable. Examples of a material for these supports include a material containing polyethylene, polypropylene, polyethylene terephthalate, polybutylene terephthalate, polyethylene naphthalate, polystyrene, nylon, cotton, acetate rayon, rayon, a rayon polyethylene terephthalate composite, polyacrylonitrile, polyvinyl alcohol, acrylic polyurethane, ester polyurethane, ether polyurethane, a styrene-isoprene-styrene copolymer, a styrene-butadiene-styrene copolymer, a styrene-ethylene-propylene-styrene copolymer, a styrene-butadiene rubber, an ethylene-vinyl acetate copolymer, cellophane, or the like as an essential component.

For the support, a material which does not adsorb a drug and does not release a drug (rivastigmine) from a side of the support is preferable. Therefore, in order to suppress adsorption and release of a drug, to improve transdermal absorbability of the drug, and to suppress occurrence of skin rash or the like, the support preferably includes one or more of the above material layers, and preferably has a moisture permeability in a specific numerical range. Specifically, the moisture permeability (JISZ0208, measured at 40° C. at 90% RH) of the support is preferably 300 g/m²·24 hr or less, particularly preferably 50 g/m²·24 hr or less. By setting the moisture permeability of the support within the above range, rivastigmine skin permeability is increased, and adequate moisture permeability can be ensured.

A form of a plastic film having excellent transparency is preferably employed in order to make the adhesive patch inconspicuous during adhesion, that is, in terms of easily making skin tone under adhesion visible. By coloring a support such as a fabric with color tone such as skin color using a coloring agent, a difference between the support and skin color can be reduced during adhesion.

The thickness of the support is usually about from 5 μm to 1 mm. When the support is a fabric, the thickness thereof is preferably from 50 μm to 1 mm, more preferably from 100 μm to 800 μm, and still more preferably from 200 μm to 700 μm. When the support is a plastic film, the thickness thereof is preferably from 10 μm to 300 μm, more preferably from 12 μm to 200 μm, and still more preferably from 15 μm to 150 μm. When the thickness of the support is as extremely thin as about 5 μm to 30 μm, it is preferable to dispose a peelable carrier film layer on a layer opposite to the adhesive layer or the rivastigmine-containing layer formed on the support because handleability of the adhesive patch is improved. When the thickness of the support is smaller than 5 μm, strength of the adhesive patch or handleability thereof is reduced, and adhesion thereof to the skin is difficult. The adhesive patch may be torn by contact with another member or the like, or may be peeled off from the skin in a short time by contact with water during bathing or the like. When the thickness of the support is too large (larger than 1 mm), the adhesive patch does not follow movement of the skin easily, and a chance to peel off the adhesive patch is easily formed around the adhesive patch. Therefore, there is a risk that the adhesive patch may be peeled off from the skin in a short time or discomfort during adhesion may be increased. When the support is a film, in order to improve an anchoring property of the adhesive and the support, one or both surfaces of the support may be subjected to a sandblasting treatment, a corona treatment, or the like. In addition, in order to facilitate removal from the packaging material (packaging bag, packaging), irregularities may be provided on one or both surfaces of the support by a method other than sandblasting.

As a support satisfying these conditions such as a drug adsorption property, moisture permeability, transparency, thickness, and the like, a polyester film is preferable, and a polyethylene terephthalate film is particularly preferable.

[Rivastigmine-Containing Drug Storage Layer]

In the rivastigmine-containing drug storage layer, rivastigmine is an essential constituent component. The rivastigmine-containing drug storage layer has a configuration in which a matrix such as a polymer contains rivastigmine. The above polymer is not particularly limited. However, a rubber or silicone polymer has a low drug holding capability, makes rivastigmine more volatile, and has a possibility of maintaining no stability. Therefore, as a polymer used for the drug storage layer, an alkyl (meth)acrylate resin is particularly preferable.

In the adhesive patch to which the present invention is directed, when a rivastigmine-containing adhesive layer described below exists, the drug storage layer is an optional layer.

Rivastigmine ((S)—N-ethyl-3-[1-(dimethylamino)ethyl]-N-methyl-phenyl-carbamate) used in the present invention has a free base form. The free base is more volatile and more unstable than an acid addition salt, and therefore is a drug to which the present invention is directed. Rivastigmine has a free base form and an acid addition salt form. When a part or the whole of the acid addition salt form rivastigmine is converted into a free base form by blending an acid compound to convert the acid addition salt into the free base form in the adhesive or the drug storage layer, the acid addition salt form rivastigmine is a drug to which the present invention is directed.

The content of rivastigmine in the drug storage layer is not particularly limited, but is, for example, from 20% to 95% by mass, preferably from 30% to 90% by mass, and more preferably from 35% to 90% by mass based on the total mass of the drug storage layer.

The blending amount of rivastigmine is, for example, from 10% to 40% by mass, preferably from 10% to 35% by mass, and more preferably from 10% to 25% by mass based on the total mass of the drug storage layer and the adhesive layer described below.

The alkyl (meth)acrylate resin contained in the rivastigmine-containing drug storage layer plays a role as a thickener. Examples thereof include an alkyl (meth)acrylate copolymer and a (meth)acrylate-containing acrylic adhesive.

The configuration of the alkyl (meth)acrylate copolymer is not particularly limited. In addition, a weight average molecular weight thereof is not particularly limited, but a copolymer of 10,000 to 300,000, preferably of 100,000 to 200,000 can be used, for example. A commercially available product can be used appropriately for these copolymers. For example, Eudragit (registered trademark, manufactured by Evonik Rohm GmbH) can be used suitably. Specific examples thereof include Eudragit E100, Eudragit EPO, Eudragit L100, Eudragit L100-55, Eudragit S100, Eudragit RL100, Eudragit RLPO, Eudragit RS100, Eudragit RSPO, and Plastoid B.

Among these Eudragit products, Eudragit EPO is particularly preferable from a viewpoint of miscibility with rivastigmine and adhesion to a support.

As a (meth)acrylate-containing acrylic adhesive, specifically, a polymer obtained by copolymerizing any one or more kinds of copolymerizable monomers (for example, 2-ethylhexyl acrylate, vinyl pyrrolidone, vinyl acetate, methoxyethyl acrylate, hydroxyethyl acrylate, or acrylic acid) using one or more kinds of alkyl (meth)acrylates as a main monomer is preferable. The alkyl (meth)acrylates can be used singly or in combination of two or more kinds thereof. For example, combination of n-butyl acrylate and methyl methacrylate can be used. A weight average molecular weight of a (meth)acrylate used for the (meth)acrylate-containing acrylic adhesive is not particularly limited, but is from 100,000 to 1,000,000.

Preferably, the above (meth)acrylate-containing acrylic adhesive substantially contains a hydroxy group and contains no component having a carboxyl group. However, even when the (meth)acrylate-containing acrylic adhesive contains a hydroxy group and contains a component having a carboxyl group, as long as the adsorption amount of a drug by a packaging bag is less than 1% in a test item of <Amount of rivastigmine adsorbed by packaging bag> described below, the (meth)acrylate-containing acrylic adhesive may contain the above component. When the (meth)acrylate-containing acrylic adhesive contains a hydroxy group and contains a component having a carboxyl group, a containing form thereof may be a state of copolymerization with a hydroxy group-containing acrylic adhesive or a state blended with the hydroxy group-containing acrylic adhesive. A hydroxy group is not included in a carboxyl group. That is, a carbonyl group is not bonded to a carbon atom to which a hydroxy group is bonded.

The content of an alkyl (meth)acrylate resin in the drug storage layer is not particularly limited, but is, for example, from 5% to 25% by mass, preferably from 5% to 20% by mass, and more preferably from 5% to 15% by mass based on the total mass of the rivastigmine-containing drug storage layer when the alkyl (meth)acrylate resin is an alkyl (meth)acrylate copolymer. The content of the alkyl (meth)acrylate resin is, for example, from 20% to 90% by mass, preferably from 30% to 85% by mass, and more preferably from 40% to 80% by mass based on the total mass of the rivastigmine-containing drug storage layer when the alkyl (meth)acrylate resin is a (meth)acrylate-containing acrylic adhesive.

The blending amount of an alkyl (meth)acrylate resin is, for example, from 0.5% to 5.0% by mass, preferably from 1.0% to 4.0% by mass, and more preferably from 1.0% to 3.0% by mass based on the total mass of the rivastigmine-containing drug storage layer and the adhesive layer described below when the alkyl (meth)acrylate resin is an alkyl (meth)acrylate copolymer. The blending amount of an alkyl (meth)acrylate resin is, for example, from 40% to 90% by mass, preferably from 50% to 90% by mass, and more preferably from 60% to 90% by mass when the alkyl (meth)acrylate resin is a (meth)acrylate-containing acrylic adhesive.

In the present invention, the rivastigmine-containing drug storage layer may further contain another additive such as a softening agent (plasticizer) or an inorganic filler, if desired.

When the rivastigmine-containing drug storage layer contains another additive, the blending amount thereof is, for example, from 0% to 30% by mass, and preferably from 0% to 20% by mass based on the total mass of the rivastigmine-containing drug storage layer. The blending amount of another additive is, for example, from 0% to 20% by mass, and preferably from 0% to 10% by mass based on the total mass of the rivastigmine-containing drug storage layer and the adhesive layer described below.

[Adhesive Layer]

In the adhesive patch to which the present invention is directed, an adhesive to constitute an adhesive layer is not particularly limited. However, a rubber or silicone adhesive has a low drug holding capability, makes rivastigmine more volatile, and has a possibility of maintaining no stability. Therefore, the adhesive layer particularly preferably contains an alkyl (meth)acrylate adhesive. The adhesive layer particularly preferably contains an acrylic adhesive containing a (meth)acrylate having a hydroxy group considering stability of rivastigmine.

As the above acrylic adhesive, specifically, a polymer obtained by copolymerizing any one or more kinds of copolymerizable monomers containing one or more kinds of hydroxy alkyl (meth)acrylates (for example, 2-ethylhexyl acrylate, vinyl pyrrolidone, vinyl acetate, methoxyethyl acrylate, hydroxyethyl acrylate, or acrylic acid) is preferable.

As the acrylic adhesive containing an acrylate having a hydroxy group, a commercially available product such as DURO-TAK (registered trademark) 87-202A, DURO-TAK 87-208A, DURO-TAK 87-2510, DURO-TAK 87-208A, DURO-TAK 87-2287, DURO-TAK 87-4287, DURO-TAK 87-2516, or DURO-TAK 87-2525 (Henkel AG&Co.) can be used suitably.

The acrylic adhesive preferably contains no acrylic adhesive having a carboxyl group substantially. Even when the acrylic adhesive contains an acrylic adhesive having a carboxyl group, the content thereof is desirably 5% by mass or less with respect to the total mass of the adhesive layer.

In the present invention, the mass ratio of the adhesive layer with respect to the total mass of the drug storage layer and the adhesive layer is, for example, from 40% to 95% by mass, preferably from 50% to 90% by mass, and more preferably from 60% to 90% by mass.

In the present invention, the adhesive layer may further contain another drug or another additive such as a tackifier, a crosslinking agent, a softener (plasticizer), an absorption accelerator, a polyhydric alcohol, a silicone oil, an inorganic filler, or an ultraviolet absorbent, if desired.

Examples of the tackifier include a terpene tackifier, a terpene phenol tackifier, a coumarone-indene tackifier, a styrene tackifier, a rosin tackifier, a xylene tackifier, a phenol tackifier, and a petroleum tackifier.

Various crosslinking agents can be further added to the adhesive layer in order to increase a cohesive force of an acrylic adhesive. Examples of the crosslinking agent include a polyfunctional isocyanate compound, a polyfunctional epoxy compound, and a polyvalent metal salt. Specifically, polyisocyanate [for example, Coronate (registered trademark) HL (hexamethylene diisocyanate HDI-TMP adduct, manufactured by Nippon Polyurethane Industry Co., Ltd.)] is preferable. As the filler, calcium carbonate, magnesium carbonate, a silicate, zinc oxide, titanium oxide, magnesium sulfate, calcium sulfate, or the like can be blended.

Examples of the absorption accelerator include a terpene oil such as d-limonene, a fatty acid ester such as glycerin monolaurate, glycerin monooleate, or diethyl sebacate, a fatty acid such as Azone, purrothiodecane, oleic acid, lauric acid, or myristic acid, and a derivative thereof.

Blending of these additives is optional. However, the blending amount of another additive is, for example, from 0% to 40% by mass, and preferably from 0% to 30% by mass based on the total mass of the adhesive layer and the drug storage layer described above.

An antioxidant is not necessarily required for the adhesive patch to which the present invention is directed. In some cases, an antioxidant has been added to a commercially available adhesive by a supplier. However, the amount thereof is usually very small, and therefore this case is defined as a case where no antioxidant is added. Examples of the antioxidant include dibutyl hydroxy toluene, tocopherol acetate, ascorbic acid, benzoic acid, paraben, benzalkonium chloride, and benzethonium chloride.

[Rivastigmine-Containing Adhesive Layer]

In the present invention, the adhesive layer may contain rivastigmine, that is, the adhesive layer may be a rivastigmine-containing adhesive layer. In this case, the above drug storage layer is an optional layer.

Also in a case of the rivastigmine-containing adhesive layer, the adhesive described in the above [Adhesive layer] can be used suitably. However, it is preferable to employ an adhesive which can be applied at a low temperature or to select an adhesive which can be applied without using a solvent in order to prevent volatilization of rivastigmine during applying an adhesive.

The rivastigmine-containing adhesive layer may further contain another additive described in the above [Adhesive layer].

The blending amount of rivastigmine is, for example, from 10% to 40% by mass, preferably from 10% to 35% by mass, and more preferably from 10% to 25% by mass based on the total mass of the rivastigmine-containing adhesive layer.

When the drug storage layer exists in addition to the rivastigmine-containing adhesive layer, the mass ratio of the rivastigmine-containing adhesive layer is, for example, from 40% to 95% by mass, preferably from 50% to 90% by mass, and more preferably from 60% to 90% by mass based on the total mass of the rivastigmine-containing adhesive layer and the drug storage layer.

[Release Paper]

Release paper used for the adhesive patch to which the present invention is directed is preferably made of a material which hardly absorbs or adsorbs a drug or the like in the adhesive. Examples thereof include a polyester film one or both surfaces of which have been subjected to a silicone treatment, polyethylene laminate fine quality paper which has been subjected to a silicone treatment, and glassine paper which has been subjected to a silicone treatment. In order to facilitate removal of release paper from the packaging material (packaging bag, packaging), irregularities can be provided on the release paper. The shape of a release liner can be a rectangle with rounded corners, a circle, or the like. The size thereof is the same as or slightly larger than that of a support having the rivastigmine-containing drug storage layer, the adhesive layer, or the rivastigmine-containing adhesive layer disposed. Release paper may be constituted by one sheet or a plurality of sheets divided. A cut line thereof may be constituted by a straight line, a wavy line, or a perforated line. Parts of the release paper may overlap each other.

[Method for Manufacturing Adhesive Patch]

The rivastigmine-containing adhesive patch to which the present invention is directed can be manufactured by the following step i) or ii).

i) A drug storage layer formation step for forming a rivastigmine-containing layer by applying a rivastigmine-containing solution on a support, an adhesive layer formation step for forming an adhesive layer by applying an acrylic adhesive-containing solution on a release liner, and an adhesive patch formation step for bonding the drug storage layer formed on the support to the adhesive layer formed on the release liner.

ii) An adhesive layer formation step for forming an adhesive layer by applying an acrylic adhesive-containing solution on a support, a drug storage layer formation step for forming a rivastigmine-containing layer by applying a rivastigmine-containing solution on a release liner, and an adhesive patch formation step for bonding the adhesive layer formed on the support to the rivastigmine-containing layer formed on the release liner.

Alternatively, for example, the adhesive patch to which the present invention is directed can be manufactured by the following step iii).

iii) An adhesive layer formation step for forming a rivastigmine-containing adhesive layer by applying an acrylic adhesive and a rivastigmine-containing solution on release paper, and an adhesive patch formation step for bonding the adhesive layer to the support.

[Administration Method]

The amount of an active ingredient (rivastigmine) to be administered in a treatment of cerebral and neuronal disorders using the adhesive patch of the present invention depends on a nature of complaints to be treated, severity thereof, and a weight of a patient. A preferable unit dose is generally from 0.25 mg to 700 mg, advantageously from 0.5 mg to 300 mg, and preferably from 1 mg to 150 mg, for example between 2 mg and 50 mg. That is, 2 mg, 5 mg, 10 mg, 15 mg, 20 mg, 25 mg, 30 mg, 40 mg, or 50 mg of product (rivastigmine) is included. This unit dose is usually administered one or more times a day, for example 2 times, 3 times, 4 times or 5 times a day, preferably 1 times to 3 times a day. An entire dose for one person per day fluctuates between 0.5 mg and 1400 mg, advantageously between 1 mg and 900 mg, for example, from 2 mg to 500 mg, more conveniently from 4 mg to 10 mg.

EXAMPLES

Hereinafter, the present invention will be described specifically by indicating Examples and Comparative Examples, but the present invention is not limited to these Examples.

Drug (rivastigmine) stability in the adhesive patch product of the present invention was evaluated based on the mixed amount of a rivastigmine decomposed product included in an adhesive patch and the adsorption amount of rivastigmine attached to a packaging bag.

[Mixed Amount of Decomposed Product]

Adhesive patch products manufactured in Examples 1 and 2 and Comparative Example 1 described below were stored under an accelerated condition (40° C.) for six months. The mixed amount of a decomposed product existing in the adhesive patch after lapse of six months was measured according to the following [Procedures for measuring mixed amount of decomposed product]. Table 1 indicates obtained results.

[Procedures for Measuring Mixed Amount of Decomposed Product]

An adhesive patch was taken out from an adhesive patch product, and release paper of the adhesive patch was peeled off. Thereafter, the adhesive patch was immersed in a sealable glass container including special grade tetrahydrofuran, and the adhesive was dissolved therein. A mixed solution of acetonitrile for a drug test/methanol for a drug test/ammonium phosphate buffer solution (pH 7.0) was added thereto to obtain a sample solution. The sample solution was analyzed by a high-performance liquid chromatography (HPLC) method.

As for the mixed amount of a decomposed product, a decomposed product peak area with respect to a peak area of rivastigmine was calculated based on the following formula, and an average value of the total amount (% by mass) of the decomposed products in three measurements as a sum of the decomposed products was calculated.

Mixed amount of decomposed product (%)=[peak area of decomposed product in sample solution/peak area of rivastigmine in standard solution*]

*standard solution: obtained by diluting a sample solution by 1/100

<Evaluation>

Evaluation was performed as follows according to the total amount of mixed decomposed products based on the obtained value.

Judgment O: the total amount of mixed decomposed products is less than 0.35%

Judgment X: the total amount of mixed decomposed products is 0.35% or more

[Adsorption Amount of Drug]

Adhesive patch products manufactured in Examples 1 and 2, Reference Example 1, and Comparative Examples 1 and 2 described below were stored under a severe condition (60° C.) for two weeks. The adsorption amount of rivastigmine by a packaging bag after lapse of two weeks was measured according to the following [Procedures for measuring content]. Table 1 indicates obtained results.

[Procedures for Measuring Content]

<Amount of Rivastigmine Remaining in Adhesive Patch>

An adhesive patch was taken out from an adhesive patch product, and release paper of the adhesive patch was peeled off. Thereafter, the adhesive patch was immersed in an internal standard solution and tetrahydrofuran for HPLC included in a sealable glass container, and the adhesive was dissolved therein. Thereafter, a mixed solution of acetonitrile for a drug/ammonium phosphate buffer solution (pH 5.8) was added thereto to prepare a sample solution (adhesive patch).

By using standard rivastigmine separately, a standard solution was prepared by a similar operation.

The sample solution and the standard solution were analyzed by a high-performance liquid chromatography (HPLC) method. The amount of rivastigmine (drug content in adhesive patch) in a sample (adhesive patch) was calculated from a ratio of a peak area of rivastigmine with respect to a peak area of an internal standard substance in each of the standard solution and the sample solution (adhesive patch).

<Amount of Rivastigmine Adsorbed by Packaging Bag>

By finely cutting a packaging bag of the adhesive patch product stored under a severe condition, a sample solution (packaging bag) was prepared according to the above procedures of <Amount of rivastigmine remaining in adhesive patch>. The amount of rivastigmine (drug content in packaging bag) in a sample (packaging bag) was calculated in similar procedures to the case using the standard solution.

<Evaluation>

From the obtained results, the drug adsorption amount (%) was calculated based on the following formula. An average value of these values in three measurements was calculated, and evaluation was performed as follows.

drug adsorption amount (%)=[drug content in packaging bag/(drug content in packaging bag+drug content in adhesive patch)]×100

Judgment O: the adsorption amount of a drug by a packaging bag is less than 1%

Judgment X: the adsorption amount of a drug by a packaging bag is 1% or more

[Peeling Strength of Adhesive Patch with Respect to Innermost Layer of Packaging Bag]

In the adhesive patch products manufactured in Example 1 and Comparative Example 3 described below, peeling strength of an adhesive patch with respect to an innermost layer of a packaging bag was measured according to [Procedures for measuring packaging material peeling strength]. Table 2 indicates obtained results.

[Procedures for Measuring Packaging Material Peeling Strength]

An adhesive patch was taken out from the adhesive patch product in each of Example 1 and Comparative Example 3, and a heat-sealed portion in a packaging bag was cut to expose an innermost layer. The adhesive patch taken out from the adhesive patch product was cut into a size of 30 mm (length)×15 mm (width) to obtain a test piece. Release paper of the test piece was peeled off under an atmosphere of temperature 23° C. and 50% RH. The test piece was lightly pressed with a finger from above on the innermost layer of the packaging bag (laminate) such that an adhesive layer of the test piece was in contact with the innermost layer of the packaging bag (laminate). Thereafter, pressure bonding was performed by performing reciprocation movement twice using a 1 kg pressure bonding roller at a rate of 600 mm/min. Immediately (within one minute) after adhesion, the test piece was peeled off from the innermost layer in the packaging bag at a peeling angle of 180 degrees and a peeling rate of 300 mm/min. Peeling strength of the test piece with respect to the innermost layer in the packaging bag was measured.

Measurement was performed five times. An average value thereof was used as peeling strength of an adhesive patch (peeling strength of adhesive patch with respect to packaging material, unit: N/15 mm) with respect to an innermost layer in a packaging bag.

Example 1

DURO-TAK (registered trademark) 87-2516 (containing a hydroxy group, Henkel AG&Co.) at 40% by mass as an acrylic adhesive and ethyl acetate at 60% were mixed at room temperature to prepare an acrylic adhesive solution (numerical value (%) was based on the total mass of the adhesive solution). Subsequently, this solution was applied on a PET film which had a thickness of 75 μm and which had been subjected to a silicone release treatment (FILMBYNA (registered trademark) 75E-0010 No. 23, manufactured by Fujimori Kogyo Co., Ltd.) such that the thickness thereof after drying was 80 μm. The resulting product was dried at 60° C. to 100° C. to form an adhesive layer.

Rivastigmine and Eudragit (registered trademark) EPO (Evonik Degussa GmbH) were weighed so as to be 90% by mass and 10% by mass, respectively, were put in a glass bottle, and were dissolved at room temperature to obtain a rivastigmine solution (numerical value (%) was based on the total mass of the rivastigmine solution). The resulting rivastigmine solution was applied on a PET film having a thickness of 25 μm (Lumirror (registered trademark) S10, manufactured by Toray Co., Ltd.) as a support so as to have a thickness of 20 μm to form a rivastigmine-containing layer.

The adhesive layer formed on the PET film which had been subjected to a silicone release treatment was bonded to the rivastigmine-containing layer formed on the PET film while the two layers face each other, and the resulting product was cut to manufacture a rectangular adhesive patch having two layers of an acrylic adhesive-containing adhesive layer and a rivastigmine-containing drug storage layer. Release paper had a rectangular shape having a size of about 1.5 times an adhesive patch, and had a linear back split in a central portion thereof. The adhesive patch was disposed in a central portion of the release paper.

The adhesive patch was enclosed in a packaging bag three sides of which had been heat-sealed while facing a laminate (refer to description below) having a layer structure obtained by laminating an EVOH film on an innermost layer side, an aluminum film, and a polyester film in this order. Subsequently, nitrogen replacement in the packaging bag was performed using a vacuum gas packaging machine. While nitrogen in the packaging bag was pushed out (discharged) by causing nitrogen to pass between two rolls, the remaining one side was heat-sealed to obtain a rectangular adhesive patch product. The obtained adhesive patch product was cut to manufacture a plurality of adhesive patch products each of which housed an adhesive patch in the packaging bag. When an oxygen concentration in the packaging bag was measured with an oxygen concentration meter, the oxygen concentration was 5% by volume.

Details of the laminate used in Examples are as follows.
lamination configuration: EVOH film/adhesive/aluminum film (AL)/adhesive/polyester film (PET)
EVOH film: ethylene unit ratio in EVOH 44% by mol, water content 0.3% to 0.5% by mass, non-stretched, thickness 30 μm
polyester film: polyethylene terephthalate film, thickness 12 μm
aluminum film: aluminum foil, thickness 7 μm
adhesive: polyurethane for adhesive Example 2

An adhesive patch product was manufactured in a similar manner to Example 1 except that the oxygen concentration in the packaging bag was 10% by volume.

Reference Example 1

An adhesive patch product was manufactured in a similar manner to Example 1 except that the packaging bag had a polypropylene film (PP, thickness 12 μm) as an innermost layer and that the oxygen concentration in the packaging bag was 10% by volume.

Comparative Example 1

An adhesive patch product was manufactured in a similar manner to Example 1 except that the packaging bag was heat-sealed without performing nitrogen replacement in the packaging bag (directly). At this time, the oxygen concentration in the packaging bag was 20.9% by volume.

Comparative Example 2

An adhesive patch product was manufactured in a similar manner to Comparative Example 1 except that the packaging bag was manufactured from a laminate having a lamination configuration of PET/AL/PET. The oxygen concentration in the packaging bag was 20.9% by volume.

Comparative Example 3

An adhesive patch product was manufactured in a similar manner to Example 1 except that the packaging bag was manufactured from a laminate having a lamination configuration of PAN/AL/PET.

TABLE 1

|  | Example 1 | Example 2 | Reference Example 1 | Comparative Example 1 | Comparative Example 2 |
|---|---|---|---|---|---|
| configuration of laminate | EVOH/AL/PET | EVOH/AL/PET | PP/AL/PET | EVOH/AL/PET | PET/AL/PET |
| oxygen concentration (% by volume) | 5 | 10 | 10 | 20.9 | 20.9 |
| mixed amount of decomposition product (total amount) [40° C., six months] | ○ | ○ | — | x | — |
| adsorption amount of drug by packaging bag [60° C., two weeks] | ○ | ○ | ○ | ○ | x |

The results in Table 1 indicate the following. That is, in Examples 1 and 2 in which a rivastigmine-containing adhesive patch was enclosed in a packaging bag constituted by a laminate having an EVOH film layer as an innermost layer and the oxygen concentration in the packaging bag was 10% by volume by replacing an inside of the packaging bag with nitrogen, a result having excellent temporal stability of rivastigmine that a mixed amount (total amount) of a rivastigmine decomposed product was small and that adsorption of a drug by the packaging bag was very small (average value 0.0%) was obtained. In Reference Example 1 having PP as an innermost layer, a result that adsorption of a drug was small (average value 0.6%) was obtained. Therefore, it was suggested that the packaging bag having PP as an innermost layer and obtained by laminating EVOH also obtained a result that the adsorption amount of rivastigmine was small. Although not indicated in Table 1, a packaging bag having a polyethylene film (PE) as an innermost layer was manufactured, and a similar experiment was performed under the same conditions (oxygen concentration 10% by volume or less). At this time, an average value of the adsorption amount was already 2.4% after lapse of seven days. It was indicated that the laminate having PE as an innermost layer had a slightly poorer suitability than PP as a packaging material for a rivastigmine-containing adhesive patch.

On the other hand, in Comparative Example 1 in which the residual oxygen concentration was more than 10% by volume without replacing an inside of the packaging bag with nitrogen, a mixed amount (total amount) of a decomposed product was large. In Comparative Example 2 in which a configuration of a laminate to form a packaging bag contains no EVOH film, a large amount of drug was adsorbed by the packaging bag. Both Comparative Examples 1 and 2 had poor results having poor temporal stability of rivastigmine.

TABLE 2

|  | Example 1 | Comparative Example 3 |
|---|---|---|
| configuration of laminate | EVOH/AL/PET | PAN/AL/PET |
| average value of packaging material peeling strength (N/15 mm) | 2.42 | 2.58 |
| standard deviation (P) | 0.12 | 0.05 |

*$P < 0.05$ (A significant difference is found): t-test

The results in Table 2 suggest that a packaging bag constituted by a laminate having an EVOH film layer as an innermost layer has smaller peeling strength than a packaging bag constituted by a laminate having a PAN film layer as an innermost layer in a case of the same adhesive patch, particularly in a case of an acrylic adhesive. This tendency was confirmed also in sensory evaluation. Therefore, the results indicate the following. That is, even when an adhesive protrudes from an adhesive patch and the adhesive which has protruded adheres to an inside of a packaging bag with time, or an adhesive layer adheres to an inside of a packaging bag by some chances when the adhesive patch is taken out from the packaging bag, in a case of the packaging bag constituted by a laminate having an EVOH film layer as an innermost layer, the adhesive (layer) can be peeled off with a lighter force than a case of the packaging bag constituted by a laminate having a PAN film layer as an innermost layer and the adhesive patch can be taken out of the packaging bag easily. The above results indicate that packaging material peeling strength is 2.5 N/15 mm or less, and preferably 2.42 N/15 mm or less.

The invention claimed is:

1. An adhesive patch product comprising a packaging bag and a rivastigmine-containing adhesive patch housed in the packaging bag, wherein
the packaging bag is formed from a laminate of at least three layers including an ethylene-vinyl alcohol copolymer film, wherein the content of an ethylene unit in the ethylene-vinyl alcohol copolymer is from 10% to 50% by mol,
the laminate has a lamination configuration having a heat-sealable ethylene-vinyl alcohol copolymer film as an innermost layer of the packaging bag, an oxygen blocking layer as a layer outside the ethylene-vinyl alcohol copolymer film, and an outer layer as a layer outside the oxygen blocking layer, or
the laminate has a lamination configuration having a sealant layer as an innermost layer of the packaging bag, an ethylene-vinyl alcohol copolymer film as a layer outside the sealant layer, an oxygen blocking layer as a layer outside the ethylene-vinyl alcohol copolymer film, and an outer layer as a layer outside the oxygen blocking layer, and
a residual oxygen concentration in the packaging bag is 10% by volume or less.

2. The adhesive patch product according to claim 1, wherein the adhesive patch includes:
a support, a rivastigmine-containing drug storage layer disposed on at least one surface of the support, an adhesive layer disposed on the drug storage layer, and release paper disposed on the adhesive layer;
a support, an adhesive layer disposed on at least one surface of the support, a rivastigmine-containing drug storage layer disposed on the adhesive layer, and release paper disposed on the drug storage layer; or
a support, a rivastigmine-containing adhesive layer disposed on at least one surface of the support, and release paper disposed on the rivastigmine-containing adhesive layer.

3. The adhesive patch product according to claim 2, wherein, in the adhesive patch,
the content of rivastigmine in the rivastigmine-containing drug storage layer is from 10% to 40% by mass based on a total mass of the drug storage layer and the adhesive layer, or
the content of rivastigmine in the rivastigmine-containing adhesive layer is from 10% to 40% by mass based on a total mass of the rivastigmine-containing adhesive layer.

4. The adhesive patch product according to claim 2, wherein the adhesive layer or the rivastigmine-containing adhesive layer contains an acrylic adhesive.

5. The adhesive patch product according to claim 1, wherein the oxygen blocking layer comprises an aluminum foil.

6. The adhesive patch product according to claim 1, wherein the laminate has the lamination configuration having the heat-sealable ethylene-vinyl alcohol copolymer film as an innermost layer of the packaging bag, the oxygen blocking layer as a layer outside the ethylene-vinyl alcohol copolymer film, and the outer layer as a layer outside the oxygen blocking layer.

7. The adhesive patch product according to claim 1, wherein no antioxidant is added to the adhesive in the rivastigmine-containing adhesive patch.

* * * * *